United States Patent
Loser

(10) Patent No.: US 7,761,941 B2
(45) Date of Patent: Jul. 27, 2010

(54) PATIENT POSITIONING TABLE FOR A TOMOGRAPHY DEVICE

(75) Inventor: Michael Loser, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 545 days.

(21) Appl. No.: 11/576,510

(22) PCT Filed: Oct. 10, 2005

(86) PCT No.: PCT/EP2005/055124

§ 371 (c)(1),
(2), (4) Date: Apr. 2, 2007

(87) PCT Pub. No.: WO2006/042803

PCT Pub. Date: Apr. 27, 2006

(65) Prior Publication Data

US 2009/0022280 A1    Jan. 22, 2009

(30) Foreign Application Priority Data

Oct. 15, 2004   (DE) ................... 10 2004 050 385

(51) Int. Cl.
*A61B 6/04* (2006.01)

(52) U.S. Cl. ............... 5/601; 5/943; 378/209

(58) Field of Classification Search ............ 5/601, 5/943; 378/209; 600/415; 108/28, 143, 108/152
See application file for complete search history.

(56) References Cited

U.S. PATENT DOCUMENTS

| | | | |
|---|---|---|---|
| 2,550,306 A | 4/1951 | Soper | |
| 5,640,958 A | 6/1997 | Bonutti | |
| 5,835,556 A | 11/1998 | Rogalla et al. | |
| 6,640,364 B1 | 11/2003 | Josephson et al. | |
| 2003/0079287 A1* | 5/2003 | Truwit | 5/601 |
| 2003/0084512 A1 | 5/2003 | Fujita et al. | |
| 2005/0060804 A1 | 3/2005 | Heinl et al. | |

FOREIGN PATENT DOCUMENTS

| | | |
|---|---|---|
| DE | 42 10 864 A1 | 10/1993 |
| DE | 101 21 130 A1 | 1/2003 |
| DE | 103 12 167 B3 | 9/2004 |

* cited by examiner

Primary Examiner—Michael Trettel
(74) Attorney, Agent, or Firm—Schiff Hardin LLP

(57) ABSTRACT

A patient positioning table for a tomography device has a table board movably mounted on a table stand. At one end of the table board, a module is attached that has a receptacle compartment therein, serving as a storage space and/or a receptacle for medical equipment. Attachments can be attached to the module for holding or mounting other items that are used in connection with a tomography procedure.

14 Claims, 3 Drawing Sheets

PATIENT POSITIONING TABLE FOR A TOMOGRAPHY DEVICE

BACKGROUND OF THE INVENTION

1. Field of the Invention

The invention concerns a patient table, in particular a patient table for a tomography apparatus.

2. Description of the Prior Art

X-ray tomography systems are generally known according to the prior art. A patient table is provided for accommodation of a patient and for step-by-step movement of the patient accommodated thereupon in a measurement device or gantry. The patient table typically has a stationary table with a movement device by means of which a table board attached thereon can be moved parallel to the longitudinal extent of the table. The table board is merely connected at its one end with the movement device such that it can be moved with its other end beyond the table into the measurement device. To avoid artifacts, the table board can be produced from a material permeable to x-rays.

In the implementation of an examination by means of x-ray computed tomography it is sometimes required to administer an infusion to the patient accommodated on the table board. Instrument for administration of the infusion, such as, for example, needles, tubes etc., are normally held ready in a separate mobile container. The mobile container also serves as a tray table for the tools or instruments, etc. An infusion container is typically accommodated on a separate stand to be provided in addition to the patient table. The provision of a mobile container as well as a stand is complicated. Apart from this, the movement of the table board can lead to an unwanted pull on the infusion tube and consequently even to the infusion needle ripping out.

In the implementation of a measurement by means of x-ray computed tomography, it can also be required to monitor specific body functions of the patient by means of a monitoring electronic, for example an EKG. Movement of the table board can also lead to an unwanted pull on cables that connect sensors attached on the body of the patient with a monitoring device arranged next to the patient table.

SUMMARY OF THE INVENTION

An object of the invention is to provide a patient table with which the disadvantages according to the prior art are avoided.

According to the invention a module fashioned in the form of a receptacle compartment is mounted at one end of the table board. The disadvantages according to the prior art can be remedied in a simpler and more cost-effective manner by the provision of the inventively proposed module at one end of the table board. First, a mobile container must no longer be provided to keep and store tools, instruments, etc. Infusion containers, monitoring electronics and the like can be accommodated in the receptacle compartment or be attached thereupon. An unwanted relative movement between such devices and the patient can consequently no longer occur. A pull on the infusion tube or on cables is safely and reliably avoided.

According to one embodiment, a handle is attached to the module, advantageously in a one-piece structure. This enables (for example in the case of a power failure) a manual displacement of the table board so that the patient can possibly leave the tomography apparatus.

According to a further embodiment, the module has a recess for accommodation of a medical monitoring device. The medical monitoring device can, for example, be an EKG device it another electronic monitoring, therapy or diagnosis device. The recess is appropriately provided with a power outlet for supplying the medical monitoring device with current. Alternatively, the receptacle compartment itself can be fashioned such that it is suitable for accommodation of a medical monitoring device. In this case the monitoring device exhibits such a large depth that the medical monitoring device can be inserted therein.

Furthermore, a cover covering the recess or the receptacle compartment can be provided. For example, the cover can serve to protect a monitoring device accommodated in the recess or in the receptacle compartment.

According to another embodiment, the receptacle compartment or a further receptacle compartment is provided on the cover. For this purpose the cover can exhibit a tablet-like depression on its external side situated opposite the recess.

in another embodiment, the table board exhibits a curvature towards the table, the curvature being transverse to its longitudinal extent. That enables a simple and exact positioning of the patient on the table board. Apart from this, a unintended lateral sliding of the patient off of the table board is made more difficult with this measure.

The module can be accommodated with positive fit on a top side of the table board facing away from the table. The invention does not require a significant change in the construction of a conventional table board. It is possible to retrofit a conventional table board with the inventive module.

According to a further embodiment, the module can be mounted on the table board such that it can be exchanged. The exchangeable attachment can be produced with conventional fastening means, for example a bolt connection and the like.

In a further embodiment the module is executed as a multifunction part. For this purpose, for example, a device for accommodation of a paper roll can be mounted on the module or can be mountable on the module. The device can be, for example, a vertical rod that can be plugged in or is plugged into the module, the vertical rod having at its free end a device for suspending fluid containers, for example an infusion bottle or an infusion pouch.

At least one of the following devices can also be provided on the module: connector socket for cables, connection for a therapy board. A therapy bed is a rigid board (for example produced from carbon fiber-reinforced plastic) with a planar surface for supporting a patient in radiation therapy.

DESCRIPTION OF THE PREFERRED EMBODIMENTS

Figure 1:
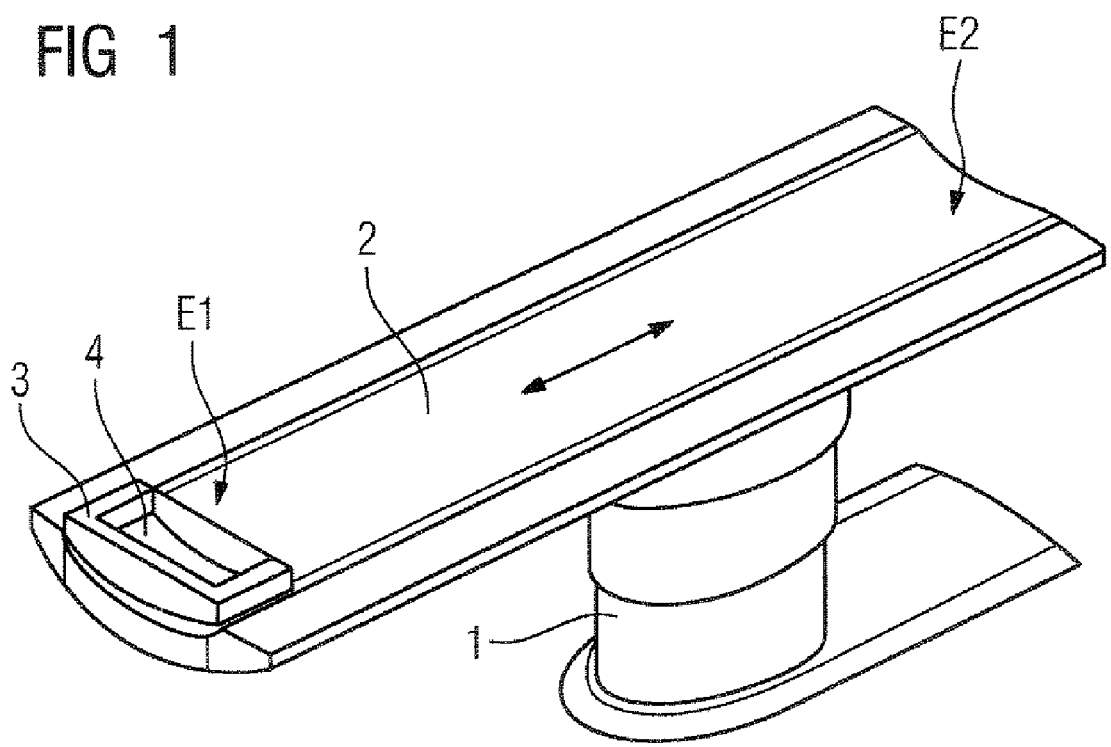
FIG. 1 is a perspective view of a patient table with a first module.

In FIGS. 1 through 7, a table board 2 movable parallel to the longitudinal extent of the table 1 is accommodated on a table 1 stationary on a base or stand. In addition a movement device (not shown here) is provided in the table 1. The table board 2 is connected with the movement device in the region of its foot-side first end E1. Outside of the fastening region at the foot-side end E1, the table board 2 has a material permeable to x-rays that can, for example, be produced from a plastic or the like. Moreover, a module 3 fashioned in the form of a receptacle compartment is mounted at the first end E1 of the table board. The module 3 can either be attached on the table board 2 or can be joined to its first end E1. It is also possible for the module 3 to be integrated with the table board 2, meaning in a one-piece design. A head-side second end of the table board 2 is designated with the reference character E2.

The module 3 is appropriately produced from plastic, for example from injection-molded plastic. It is provided with a receptacle compartment 4 that is bordered by four circumferential walls and a base or bottom.

The module 3 is rigidly connected with the table board 2, for example by means of bolts (not shown here) or the like. Given a movement of the table board 2, the module 3 (as a component of the table board 2) moves along with this relative to the table 1.

The module 3 can be provided with a handle (not shown here) with which the table board 2 can, for example, be manually displaced back and forth relative to the table 1 in the event of a power outage.

Figure 2:
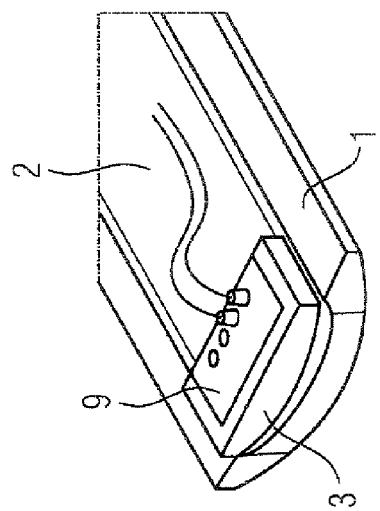
FIG. 2 is a perspective partial view of a first embodiment of the module according to FIG. 1.

FIG. 2 shows a first embodiment of the module 3. A retainer 5 (produced, for example, from metal) for suspended accommodation of an infusion container is thereby inserted into the module 3. However, it is advantageously mounted such that it can be detached from the module 3, for example inserted into a suitable blind hole.

Figure 3:
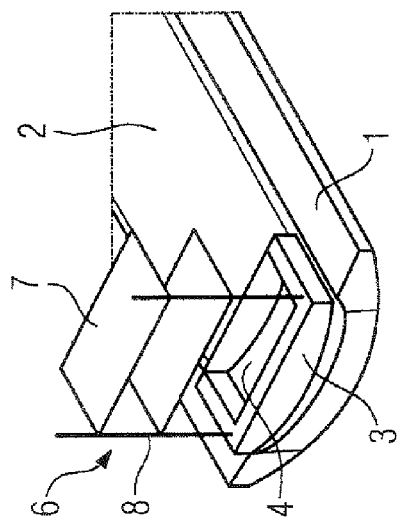
FIG. 3 is a perspective partial view of a second embodiment of the module according to FIG. 1.

In the second embodiment shown in FIG. 3 a rack 6 is attached on the module 3. The rods 8 supporting the rack shelves 7 are inserted into recesses (not shown here) provided for this at the module 3.

Figure 4:
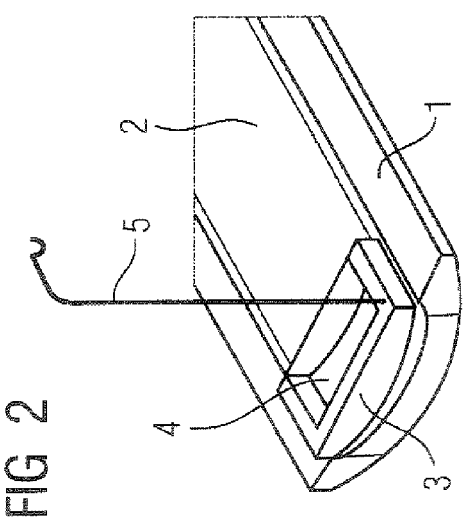
FIG. 4 is a perspective partial view of a third embodiment of the module according to FIG. 1.

A cover 9 with which the attachment tray 4 can be closed is provided in the third embodiment shown in FIG. 4. As is apparent from FIG. 4, the cover 9 can, for example, be provided with connectors for termination of cables. The cover 9 can be attached such that it can lock or close on the module 3, such that with this the deposition compartment 4 can be firmly sealed.

Figure 5:
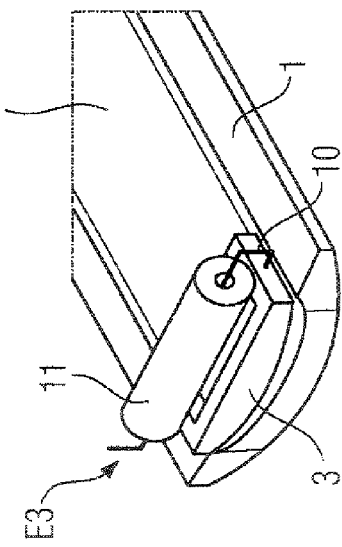
FIG. 5 is a perspective partial view of a fourth embodiment of the module according to FIG. 1.

In the fourth embodiment shown in FIG. 5 a paper role retainer 10 (executed in the form of a metal bracket) is attached to the module 3 to the module 3. The bracket 10 has a free third end E3 which enables a mounting of a paper roll 11.

Figure 6:
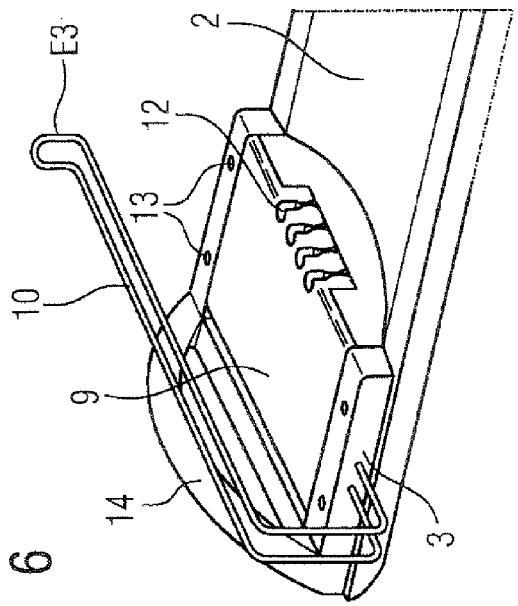
FIG. 6 is a perspective partial view of a fifth embodiment of the module according to FIG. 1.

FIG. 6 shows the module 3 in a multifunctional embodiment. The paper roll retainer 10 as well as the cover 9 are again recognizable. In the shown embodiment of the cover 9, openings in for passing cables are provided therein. Recesses 13, for example, for insertion of the retainer 5 shown in FIG. 2 or the rods 8 shown in FIG. 3, are also provided in the short walls situated opposite one another. The module 3 here moreover has a handle 14 that is advantageously produced in a one-piece design with the module 3.

A conventional mobile container and/or stands for accommodation of an infusion container can in particular be foregone with the multifunctional module 3 shown in FIG. 6. The component 3 can be produced relatively cost-effectively. A relative movement between an infusion container accommodated on the module 3 and/or electrical monitoring devices provided in the deposition compartment 4 is advantageously avoided.

Figure 7:
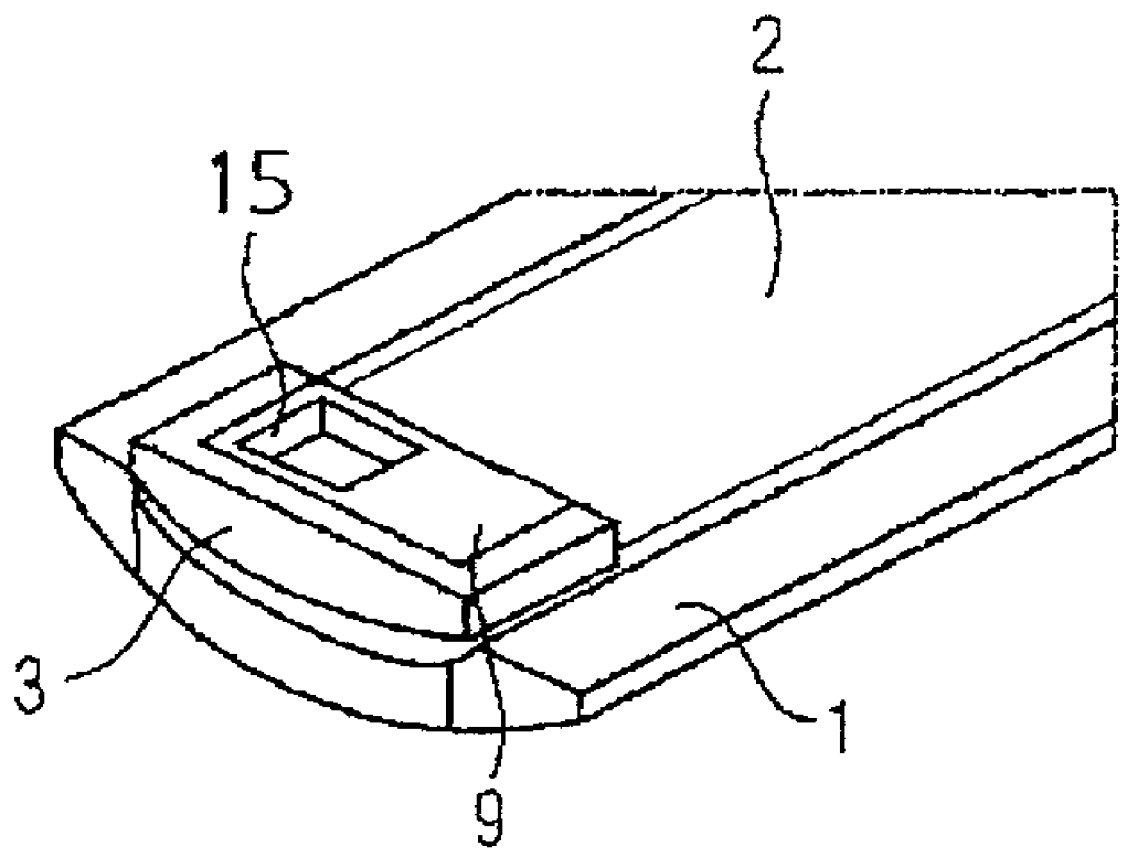
FIG. 7 is a perspective partial view of a sixth embodiment of the module according to FIG. 1.

FIG. 7 shows the module 3 in a further embodiment, wherein the cover 9 has a further receptacle 15 therein.

Although modifications and changes may be suggested by those skilled in the art, it is the invention of the inventor to embody within the patent warranted heron all changes and modifications as reasonably and properly come within the scope of his contribution to the art.

I claim as my invention:

1. A patient table for a tomography apparatus comprising:
    a table base;
    a table board having a longitudinal axis, said table board being mounted on said table base and being movable relative to said table base along said longitudinal axis, said table board having opposite ends spaced from each other along said longitudinal axis and a table surface between said opposite ends;
    a module having a receptacle compartment therein, said module being a component separate from said table board and having a bottom having a shape conforming to said table surface, said module having a handle thereon allowing manual gripping thereof to manually move said table board relative to said table base; and
    attachment elements rigidly, but detachably, attaching said module to said table board with said module bottom adjacent said table surface at one of said ends of said table board.

2. A patient table as claimed in claim 1 wherein said module receptacle compartment is a recess configured to receive a medical monitoring device.

3. A patient table as claimed in claim 2 comprising a cover covering said recess.

4. A patient table as claimed in claim 3 wherein said cover contains a further receptacle compartment therein.

5. A patient table as claimed in claim 1 wherein said receptacle compartment is configured to receive a medical monitoring device.

6. A patient table as claimed in claim 5 comprising a cover covering said receptacle compartment.

7. A patient table as claimed in claim 6 wherein said cover comprises a further receptacle compartment therein.

8. A patient table as claimed in claim 1 wherein said table surface of said table board has a curvature proceeding transversely to said longitudinal axis of said table board.

9. A patient table as claimed in claim 1 comprising a paper roll holder attached to said module.

10. A patient table as claimed in claim 9 wherein said paper roll holder is detachably attached to said module.

11. A patient table as claimed in claim 1 comprising a holder for suspending a fluid container attached to said module.

12. A patient table as claimed in claim 11 wherein said holder is detachably attached to said module.

13. A patient table as claimed in claim 1 wherein said module comprises a connector socket for electrical cables.

14. A patient table as claimed in claim 1 wherein said module comprises a connection for a therapy board.

* * * * *